United States Patent [19]

Kleiner

[11] Patent Number: 4,886,628

[45] Date of Patent: Dec. 12, 1989

[54] PROCESS FOR THE PREPARATION OF AMINOCARBONYLMETHANOIC ACIDS OF PHOSPHORUS

[75] Inventor: Hans-Jerg Kleiner, Kronberg/Taunus, Fed. Rep. of Germany

[73] Assignee: Hoechst Aktiengesellschaft, Frankfurt am Main, Fed. Rep. of Germany

[21] Appl. No.: 262,110

[22] Filed: Oct. 19, 1988

Related U.S. Application Data

[63] Continuation of Ser. No. 165,534, Mar. 8, 1988, abandoned.

[30] Foreign Application Priority Data

Mar. 10, 1987 [DE] Fed. Rep. of Germany ....... 3707638

[51] Int. Cl.$^4$ ............................. C07F 9/30; C07F 9/38
[52] U.S. Cl. ........................................................ 56/15
[58] Field of Search .................................... 260/502.56

[56] References Cited

U.S. PATENT DOCUMENTS

| | | | |
|---|---|---|---|
| 2,620,327 | 12/1952 | Albisetti | 564/129 |
| 2,938,053 | 5/1960 | Blake et al. | 564/129 |
| 3,098,865 | 7/1963 | Schimmelschmidt et al. | 260/543 P |
| 3,579,576 | 5/1971 | Angstodt | 260/543 P |

OTHER PUBLICATIONS

Wagner et al, "Synthetic Organic Chemistry", p. 570 (1953).
Kosolspoff, "Organophosphorus Compounds", pp. 138 and 139 (1950).

Primary Examiner—J. E. Evans

[57] ABSTRACT

A process for the preparation of aminocarbonyl acids of phosphorus of the general formula I

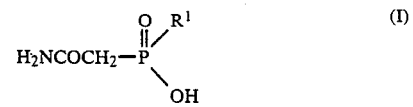

wherein $R^1$ means OH or $C_1$-$C_3$-alkyl which comprises reacting a cyano halide of phosphorus of the general formula II

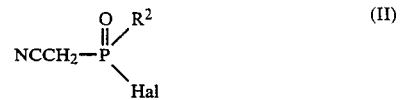

with at least the stoechiometric amount of water, in formula II $R^2$ meaning a halogen having an atomic weight in the range of from 35 to 80 or $C_1$-$C_3$-alkyl and Hal being a halogen having anatomic weight in the range of from 35 to 80.

19 Claims, No Drawings

PROCESS FOR THE PREPARATION OF AMINOCARBONYLMETHANOIC ACIDS OF PHOSPHORUS

This application is a continuation of our copending, application Ser. No. 07/165,534, filed Mar. 8, 1988, now abandoned.

Aminocarbonylmethanephosphonic acid and alkylaminocarbonylmethylphosphinic acids are valuable intermediate products for the preparation of aminomethanephosphonic acid and alkylaminomethylphosphinic acids (see European Published Specification No. 0,184,753 and European Published Specification No. 242,706). Aminocarbonylmethanephosphonic acid in particular has hitherto not been easy of access. Hitherto, only the hydrolysis of bis-(trimethylsilyl) aminocarbonylmethanephosphonate has been described for its preparation (see European Published Specification No. 242,706). Further processes for its preparation are therefore greatly desired.

It has now been found, surprisingly, that aminocarbonylmethanephosphonic acid and alkylaminocarbonylmethylphosphinic acids of the general formula I (see patent claim 1) in which $R^1$ denotes OH or $C_1$-$C_3$-alkyl can be prepared in a simple and advantageous manner by reacting a cyanomethanephosphonic acid dihalide or alkyl cyanomethylphosphinic acid halide, respectively, corresponding to the general formula (see patent claim 1) in which $R^2$ means a halogen having an atomic weight of 35-80 or $C_1$-$C_3$-alkyl and Hal denotes a halogen having an atomic weight of 35 to 80, which at least a stoichiometric amount of water. The cyano group is thus co-hydrolysed virtually completely in this process.

The acid halides used, in particular cyanomethanephosphonic acid dichloride and cyanomethylmethylphosphinic acid chloride can be obtained by the process of U.S. patent application . . . Ser. No. 165,581, filed Mar. 8, 1988 of the same date. It is advantageous to carry out the process according to the invention at temperatures from $-30°$ to $+100°$ C., preferably from $-5°$ to $+50°$ C.

The term "stoichiometric amount" is to be understood as meaning the amount of water which is required by stoichiometry for the hydrolysis of the halogen atoms and of the cyano group to give the amide group. In general therefore at least 3 moles of water are employed for one mole of cyanomethanephosphonic acid dihalide and, in general, at least 2 moles of water for one mole of alkylcyanomethylphosphinic acid halide, this water being optionally in the form of an aqueous hydrogen halide acid, such as hydrochloric acid, of various concentrations, which facilitates working in the lower temperature ranges. In addition to hydrochloric acid, aqueous solutions of the other hydrogen halides, such as hydrogen bromide or hydrogen fluoride, are also suitable for this purpose. An excess of water, for example up to two or three times the stoichiometric amount, is possible.

It is also possible to add water-miscible solvents which are inert towards the reactants under the reaction conditions, in order to ensure that the system can be filtered with suction. Examples of suitable solvents are low-molecular aliphatic carboxylic acids, such as formic acid and acetic acid, and ketones, such as acetone, methyl ethyl ketone and methyl isobutyl ketone. The use of alcohols, such as isopropanol or isobutanol, for digestion is also possible.

It is advantageous to meter the water slowly into the acid halide, for example to add it dropwise. The process can, however, be carried out in the reverse sequence. Prolonged subsequent stirring is advantageous in order to complete the reaction. The alkyl radicals can be methyl, ethyl, propyl or isopropyl; methyl is preferred. The acids prepared in accordance with the invention are obtained in a crystalline form. However, the phosphinic acids in particular retain the hydrogen halide to a greater or lesser extent. They are thus contaminated with hydrogen halide. Removal of the adhering hydrogen halide is possible, for example by recrystallization. The hydrogen halide can also be removed by heating under reduced pressure.

EXAMPLES (1) A total of 20 g (1.11 mol) of water were added dropwise in the course of 2 hours, at an initial temperature of 0°–5° C. and with stirring, to 54.5 g (0.35 mol) of cyanomethanephosphonic acid dichloride. After half the material had been added dropwise, the reaction material become difficult to stir; further dropwise addition was therefore made without further cooling, until the temperature had risen to approx. 30° C. At the same time hydrogen chloride was evolved as an exit gas. Dropwise addition was concluded at 30° C. The mixture was then stirred for a fairly long time until the reaction material had crystallized completely. 150 ml of glacial acetic acid were then added and the mixture was vigorously stirred and then filtered with suction. 43 g of aminocarbonylmethanephosphonic acid of melting point 176° C. were obtained. A further 2.5 g were isolated from the filtrate by concentrating the latter. On the basis of a $^{31}$P-NMR spectrum, the purity was 99.3%. The total yield was accordingly 94% of theory.

(2) 54.5 g (0.35 mol) of cyanomethanephosphonic acid dichloride were added dropwise in the course of 2 hours, at 0° C. and with vigorous cooling, to 31.3 g (1.1 mol, relative to the water content) of concentrated hydrochloric acid; hydrogen chloride was evolved in the course of this as an exit gas. Stirring was then continued, first at 5° C. and then at room temperature, until the reaction material was crystalline. 150 ml of glacial acetic acid were then added and the mixture was vigorously stirred and then filtered with suction. 41 g of aminocarbonylmethanephosphonic acid of melting point 174°–175° C. were obtained. A further 2.5 g were isolated from the filtrate. The total yield was accordingly 90% of theory.

(3) 73.5 g (0.535 mol) of cyanomethylmethylphosphinic acid chloride were added dropwise in the course of 2.5 hours, at 0°–5° C. and with vigorous stirring, to 32.4 g (1.14 mol, relative to the water content) of concentrated hydrochloric acid, hydrogen chloride being evolved; stirring was then continued at 5° C. and finally at room temperature until the reaction material had crystallized completely. Isopropanol was then added and the mixture was stirred vigorously and then filtered with suction. 65 g of crude aminocarbonylmethylmethylphosphinic acid containing 8.5% of hydrogen chloride were obtained. It was possible to isolate a further 10 g of crude product from the filtrate. The whole of the crude product was dried at 110° C./0.067 kPa in a drying pistol. 64 g of aminocarbonylmethylmethylphosphonic acid with a hydrogen chloride content of 0.2% and melting point 121°–125° C. were obtained; after

I claim:

1. A process for the preparation of aminocarbonyl acids of phosphorus of the general formula I

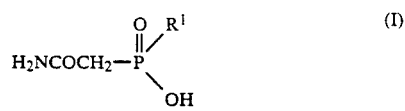

wherein $R^1$ means OH or $C_1$–$C_3$ alkyl which comprises reacting at a temperature in the range of from $-30°$ to $+100°$ C. a cyano halide of phosphorus of the general formula II

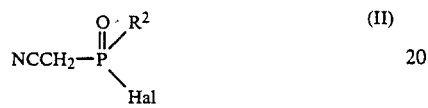

with substantially the stoichiometric amount of water, in formula II $R^2$ meaning a halogen having an atomic weight in the range of from 35 to 80 or a $C_1$–$C_3$ alkyl and Hal being a halogen having an atomic weight in the range of from 35 to 80.

2. A process as claimed in claim 1, wherein Hal means chlorine.

3. A process as claimed in claim 2, wherein cyanomethane phosphonic acid dichloride is used as the starting material.

4. A process as claimed in claim 2, wherein cyanomethylmethyl-phosphinic acid chloride is used as the starting material.

5. A process as claimed in claim 1, which is carried out at a temperature in the range of from $-5°$ to $+50°$ C.

6. A process as claimed in claim 1, wherein the water is applied in the form of an aqueous hydrohalic acid.

7. A process as claimed in claim 6, wherein the water is applied in the form of aqueous hydrochloric acid.

8. A process as claimed in claim 1, wherein there is added in addition to water at least one water-miscible solvent inert towards the reactants under the reaction conditions.

9. A process as claimed in claim 8, wherein the solvent is a low-molecular aliphatic carboxylic acid.

10. A process as claimed in claim 11, wherein the solvent is acetic acid.

11. A process as claimed in claim 1, wherein in formula I $R^1$ means methyl.

12. A process for the preparation of aminocarbonyl acids of phosphorus of the general formula I

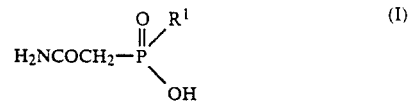

wherein $R^1$ means OH or $C_1$–$C_3$-alkyl which comprises reacting at a temperature in the range of from $-30°$ to $+100°$ C. a cyano halide of phosphorus of the general formula II

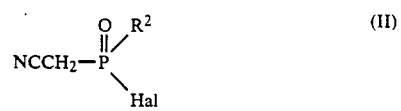

with at least the stoichiometric and up to the double of the stoichiometric amount of water, in formula II $R^2$ meaning a halogen having an atomic weight in the range of from 35 to 80 or a $C_1$–$C_3$-alkyl and Hal being a halogen having an atomic weight in the range of from 35 to 80.

13. A process as claimed in claim 12, which is carried out at a temperature in the range of from $-5°$ to $+50°$ C.

14. A process as claimed in claim 12, wherein cyanomethane phosphonic acid dichloride is used as the starting material.

15. A process as claimed in claim 12, wherein cyanomethylmethyl-phosphinic acid chloride is used as the starting material.

16. A process as claimed in claim 12, wherein in formula I $R^1$ means methyl.

17. A process as claimed in claim 12, wherein there is added acetic acid in addition to water as a water-miscible solvent inert towards the reactants under the reaction conditions.

18. A process as claimed in claim 12, wherein the reaction is carried out by adding the water to the compound of formual II.

19. A process as claimed in claim 1, wherein the reaction is carried out by adding the water to the compound of formula II.

* * * * *

UNITED STATES PATENT AND TRADEMARK OFFICE
CERTIFICATE OF CORRECTION

PATENT NO.  : 4,886,628
DATED       : December 12, 1989
INVENTOR(S) : Hans-Jerg Kleiner It is certified that error appears in the above-identified patent and that said Letters Patent is hereby corrected as shown below:

In Claim 10, Column 4, line 1,

"A process as claimed in claim 11" should read

-- A process as claimed in claim 9 -- .

Signed and Sealed this

Ninth Day of July, 1991

*Attest:*

HARRY F. MANBECK, JR.

*Attesting Officer*     *Commissioner of Patents and Trademarks*